United States Patent [19]
Charpentier

[11] Patent Number: 6,057,341
[45] Date of Patent: *May 2, 2000

[54] BI-AROMATIC DIBENZOFURAN DERIVATIVES AND THEIR USE IN HUMAN AND VETERINARY MEDICINE AND IN COSMETICS

[75] Inventor: Bruno Charpentier, Biot, France

[73] Assignee: Centre International de Recherches Dermatologiques Galderma, Valbonne, France

[*] Notice: This patent is subject to a terminal disclaimer.

[21] Appl. No.: 09/091,813
[22] PCT Filed: Oct. 20, 1997
[86] PCT No.: PCT/FR97/01878
  § 371 Date: Sep. 4, 1998
  § 102(e) Date: Sep. 4, 1998
[87] PCT Pub. No.: WO98/17659
  PCT Pub. Date: Apr. 30, 1998

[30] Foreign Application Priority Data

Oct. 23, 1996 [FR] France ................. 95/12914

[51] Int. Cl.[7] .......... A61K 31/455; A61K 31/34; C07D 307/79; C07D 311/78; C07D 405/00
[52] U.S. Cl. .......... 514/337; 514/422; 514/444; 514/468; 546/196; 546/284.1; 548/525; 549/60; 549/383
[58] Field of Search ................. 514/337, 422, 514/444, 468; 546/196, 284.1; 548/525; 549/60, 383

[56] References Cited

U.S. PATENT DOCUMENTS 5,702,710  12/1997  Charpentier et al. ........... 424/401
5,747,530   5/1998  Charpentier et al. ........... 514/468

FOREIGN PATENT DOCUMENTS 0 708 100  4/1996  European Pat. Off. .
0 709 382  5/1996  European Pat. Off. .

Primary Examiner—Ba K. Trinh
Attorney, Agent, or Firm—Burns, Doane, Swecker & Mathis, L.L.P.

[57] ABSTRACT

The invention concerns novel bi-aromatic dibenzofuran derivatives of formula (I),and their use in pharmaceutical compositions for human or veterinary medicine (skin, rheumatic respiratory, cardiovascular, and ophthalmologic disorders), or in cosmetic compositions as well. The X, Ar, $R_1$ and $R_2$ in formula (I) are defined in the specification.

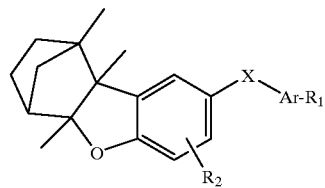

(I)

17 Claims, No Drawings

BI-AROMATIC DIBENZOFURAN DERIVATIVES AND THEIR USE IN HUMAN AND VETERINARY MEDICINE AND IN COSMETICS

This is a 371 application of PCT/FR97/01878 dated Oct. 20, 1997.

The present invention relates, as novel and useful industrial products, to biaromatic compounds simultaneously exhibiting a lipophilic unit derived from 1,2,3,4,4a,9b-hexahydro-1,4a,9b-trimethyl-1,4-methanodibenzofuran connected to a second aromatic nucleus via a linker containing 3 bonds, The compounds obtained exhibit pharmacological responses of retinoid agonist type, characterized by a marked effect in the fields of cell differentiation and proliferation.

The present invention also relates to the use of these novel compounds in pharmaceutical compositions intended for use in human or veterinary medicine or else in cosmetic compositions.

As the compounds according to the invention exhibit an activity in cell proliferation and differentiation, they can consequently be used in the topical and systemic treatment of dermatological conditions linked to a disorder of keratinization, dermatological conditions (or others) having an inflammatory, viral and/or immunoallergic component, and dermal or epidermal proliferations, whether benign or malignant. These compounds can additionally be used in the treatment of degenerative diseases of the connective tissue, for controlling ageing of the skin, whether photoinduced or chronologic, and treating disorders of cicatrization. Finally, they find an application in the ophthalmological field, in particular in the treatment of corneopathies. Furthermore, the compounds according to the invention can find an application in the field of osteoporosis. Finally, they can generally find an application in the treatment of any disease which is associated with a modification in the expression of the receptors of the superfamily of the nuclear receptors for thyroid and steroid hormones.

They can also be used in cosmetic compositions for body or hair hygiene.

Antagonists of retinoic acid are known comprising a lipophilic part derived from 1,2,3,4,4a,9b-hexahydro-1,4a, 9b-trimethyl-1,4-methanodibenzofuran and a linker comprising 4 free bonds or bonds included within a ring (EP 708,100 and EP 709,382).

It is also known, to date, that the change from an agonist retinoid structure to antagonist retinoid structure requires the introduction of well defined modifications into the lipophilic part (A. Nadzan, Annual report in medicinal chemistry, 1995, vol. 30, 119; M. Teng, T et al., J. Medicinal Chemistry, 1996, vol. 39, 3035; C. Apfel et al., Proceedings of National Academy of Sciences, USA, 1992, vol. 89, 7129).

The Applicant Company has now just found, surprisingly and contrary to what was established until now, that the modification alone of the linker (chemical unit comprising a sequence containing three bonds, in this case) makes it possible to change from an antagonist activity to an agonist activity, without, furthermore, other modifications.

The compounds according to the invention are represented by the following general formula (I):

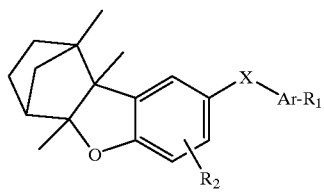

in which,

Ar represents one of the following radicals:

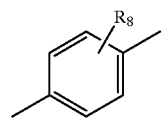

(a)

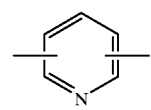

(b)

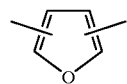

(c)

(d)

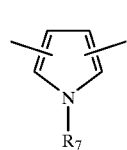

(e)

$R_7$ and $R_8$ being defined hereinbelow, X represents the following bonds of formula (a)–(g), which can be read in both directions:

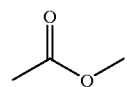

(a)

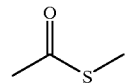

(b)

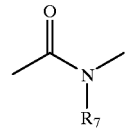

(c)

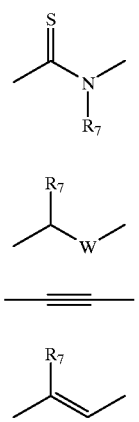

W and R<sub>7</sub> being defined hereinbelow,
$R_1$ represents
(i) a hydrogen atom,
(ii) the —$CH_3$ radical,
(iii) the —O—$R_3$ radical,
(iv) the —$CH_2$—O—$R_3$ radical,
(v) the —O$(CH_2)_m$—$(CO)_n$—$R_4$ radical,
(vi) the —CO—$R_5$ radical
(vii) the —CO—O—$R_6$ radical
$R_2$ represents a hydrogen atom or the —$(CH_2)_n$—O—$R_3$ radical,
m and n as well as $R_3$ to $R_6$ being defined below,
W represents the oxygen atom, the $S(O)_p$ radical or the N—$R_7$ radical, $R_7$ being defined hereinbelow,
$R_3$ represents a hydrogen atom, a lower alkyl radical or a —CO—$R_9$ radical, $R_9$ being defined hereinbelow,
$R_4$ represents a lower alkyl radical or a heterocycle,
$R_5$ represents a hydrogen atom, a lower alkyl radical or an —N(r',r'') radical,
in which r' and r'', which are identical or different, represent a hydrogen atom, a lower alkyl radical, a mono- or polyhydroxyalkyl radical, an optionally substituted aryl radical or an amino acid, peptide or sugar residue or alternatively r' and r'', taken together, form a heterocycle,
R6 represents a hydrogen atom, a linear or branched alkyl radical having from 1 to 20 carbon atoms, an alkenyl radical, a mono- or polyhydroxyalkyl radical, an optionally substituted aryl or aralkyl radical, or a sugar or amino acid or peptide residue,
$R_7$ represents a hydrogen atom or a lower alkyl radical,
$R_8$ represents the —$(CH_2)_n$—O—$R_3$ radical, $R_3$ being defined hereinabove,
$R_9$ represents a hydrogen atom, a lower [lacuna] radical or an aryl radical,
m is an integer equal to 1, 2 or 3,
n is an integer equal to 0 or 1,
and the optical and geometrical isomers of the said pure compounds or their mixtures in any proportion and their pharmaceutically acceptable salts.

The pharmaceutically acceptable salts are in particular addition salts with a standard acid or a standard base. When the compounds according to the invention are provided in the form of salts by addition of a base, it concerns salts of an alkali metal or alkaline earth metal or alternatively of zinc or of an organic amine. When the compounds are provided in the form of salts by addition of an acid, it concerns pharmaceutically or cosmetically acceptable salts obtained by addition of an inorganic or organic acid, in particular hydrochloric, sulphuric, acetic, citric, fumaric, hemisuccinic, maleic and mandelic acid.

Lower alkyl radical is understood to mean a radical having from 1 to 12 carbon atoms which can be linear or branched and preferably the methyl, ethyl, isopropyl, butyl and tert-butyl, hexyl, nonyl and dodecyl radicals.

Alkyl radical is understood to mean a linear or branched radical having from 1 to 20 carbon atoms, in particular the methyl, ethyl, isopropyl, butyl and tert-butyl, hexyl, nonyl and dodecyl, hexadecyl and octadecyl radicals.

Alkenyl radical is understood to mean a linear or branched radical having from 1 to 20 carbon atoms exhibiting a double bond.

Monohydroxyalkyl radical must be understood as meaning a radical having from 1 to 6 carbon atoms, in particular a 2-hydroxyethyl, 2-hydroxypropyl or 3-hydroxypropyl radical.

Polyhydroxyalkyl radical must be understood as meaning a radical containing from 2 to 6 carbon atoms and from 2 to 5 hydroxyl groups, such as the 2,3-dihydroxypropyl, 2,3,4-trihydroxybutyl and 2,3,4,5-tetrahydroxypentyl radicals or the pentaerythritol residue.

Optionally substituted aryl radical must be understood as meaning a phenyl radical optionally substituted by one or more halogen atoms, a hydroxyl functional group or nitro functional group, or a methoxy group.

Amino acid residue must be understood as meaning a residue deriving, for example, from one of the 20 amino acids of L or D configuration from which mammalian proteins are constructed. Peptide residue must be understood as meaning a linear peptide containing 2 to 10 amino acids.

Sugar residue must be understood as meaning a residue deriving, for example, from glucose, galactose, mannose or glucuronic acid.

Heterocycle is preferably understood as meaning a piperidino, morpholino, pyrrolidino or piperazino radical, optionally substituted in the 4-position by a $C_1$–$C_6$ alkyl radical or a mono- or polyhydroxyalkyl radical, as defined hereinabove.

Mention may in particular be made, among the compounds of formula (I) hereinabove coming within the scope of the present invention, of the following:

Ethyl 2-[(E)-2-(1,2,3,4,4a,9b-hexahydro-1,4a,9b-trimethyl-1,4-methanodibenzofuran-8-yl)-1-propenyl]-4-thiophenecarboxylate 2-[(E)-2-(1,2,3,4,4a,9b-Hexahydro-1,4a,9b-trimethyl-1,4-methanodibenzofuran-8-yl)-1-propenyl]-4-thiophenecarboxylic acid 2-[(E)-2-(1,2,3,4,4a,9b-Hexahydro-1,4a,9b-trimethyl-1,4-methanodibenzofuran-8-yl)-1-propenyl]-5-thiophenecarboxylic acid 6-[(E)-2-(1,2,3,4,4a,9b-Hexahydro-1,4a,9b-trimethyl-1,4-methanodibenzofuran-8-yl)-1-propenyl]nicotinic acid Methyl 4-[3-(1,2,3,4,4a,9b-hexahydro-1,4a,9b-trimethyl-1,4-methanodibenzofuran-8-yl)ethynyl]benzoate 4-[3-(1,2,3,4,4a,9b-Hexahydro-1,4a,9b-trimethyl-1,4-methanodibenzofuran-8-yl)ethynyl]benzoic acid 4-[-2-(1,2,3,4,4a,9b-Hexahydro-1,4a,9b-trimethyl-1,4-methanodibenzofuran-8-yl)ethynyl]-2-thiophenecarboxylic acid 6-[-2-(1,2,3,4,4a,9b-Hexahydro-1,4a,9b-trimethyl-1,4-methanodibenzofuran-8-yl)ethynyl]nicotinic acid Methyl 4-[3-(1,2,3,4,4a,9b-hexahydro-1,4a,9b-trimethyl-1,4-methanodibenzofuran-8-yl)carbonyloxy]benzoate 4-[3-(1,2,3,4,4a,9b-Hexahydro-1,4a,9b-trimethyl-1,4-methanodibenzofuran-8-yl)carbonyloxy]benzoic acid Benzyl 4-[(1,2,3,4,4a,9b-hexahydro-1,4a,9b-trimethyl-1,4-methanodibenzofuran-8-yl)carboxamido]benzoate 4-[(1,2,3,4,4a,9b-Hexahydro-1,4a,9b-trimethyl-1,4-methanodibenzofuran-8-yl)carboxamido]benzoic acid Methyl 6-[(1,2,3,4,4a,9b-hexahydro-1,4a,9b-trimethyl-1,4-methanodibenzofuran-8-yl)carboxamido]-2-hydroxybenzoate 6-[(1,2,3,4,4a,9b-Hexahydro-1,4a,9b-trimethyl-1,4-methanodibenzofuran-8-yl)carboxamido]-2-hydroxybenzoic acid Methyl 4-[(1,2,3,4,4a,9b-hexahydro-1,4a,9b-trimethyl-1,4-methanodibenzofuran-8-yl)thiocarboxamido]benzoate acid 4-[(1,2,3,4,4a,9b-Hexahydro-1,4a,9b-trimethyl-1,4-methanodibenzofuran-8-yl)thiocarboxamido]benzoic acid.

Among the compounds of formula (I) hereinabove, preference is given to the compounds corresponding to the following general formula (Ia)

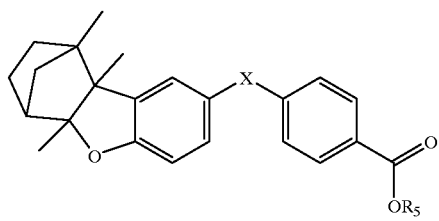

(Ia)

in which,
X has the meaning (c), (d), (f) or (g),
(c), (d), (f), (g) and $R_6$ being defined above.

The methods for the preparation of the compounds of general formula (I) are illustrated in the following.

The compounds of formula Ib are prepared from aldehyde or ketone derivatives of formula II according to a Wittig or Horner-Emmons reaction as indicated in the scheme hereinbelow:

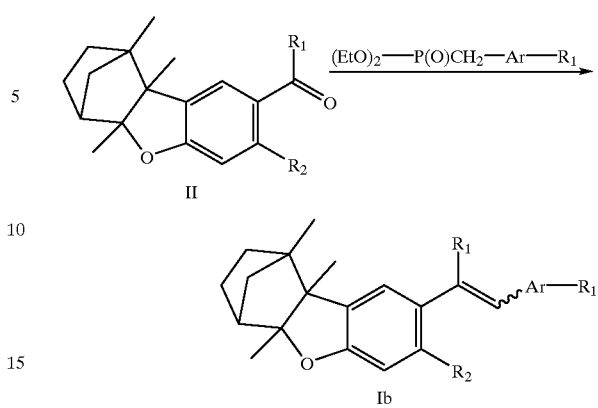

The acetylenic derivatives Ic can be prepared according to three different methods, as indicated in FIG. 1 hereinbelow:

either by conversion of the brominated derivative III into the aldehyde compound IV and then conversion of the aldehyde into the dibromostyrene derivative V with carbon tetrabromide and triphenylphosphine. This compound is then converted into the triple bond by the action of a base, such as n-butyllithium, in an aprotic solvent, such as tetrahydrofuran;

or by conversion of the brominated derivative III into the trimethylsilylacetylenic derivative VI and then desilylation in the presence either of potassium carbonate or of tetrabutylammonium fluoride;

or from the methyl ketone derivative X, which is then treated with lithium diisopropylamide (LDA), then a dialkyl phosphate chloride and again with LDA;

FIG. 1

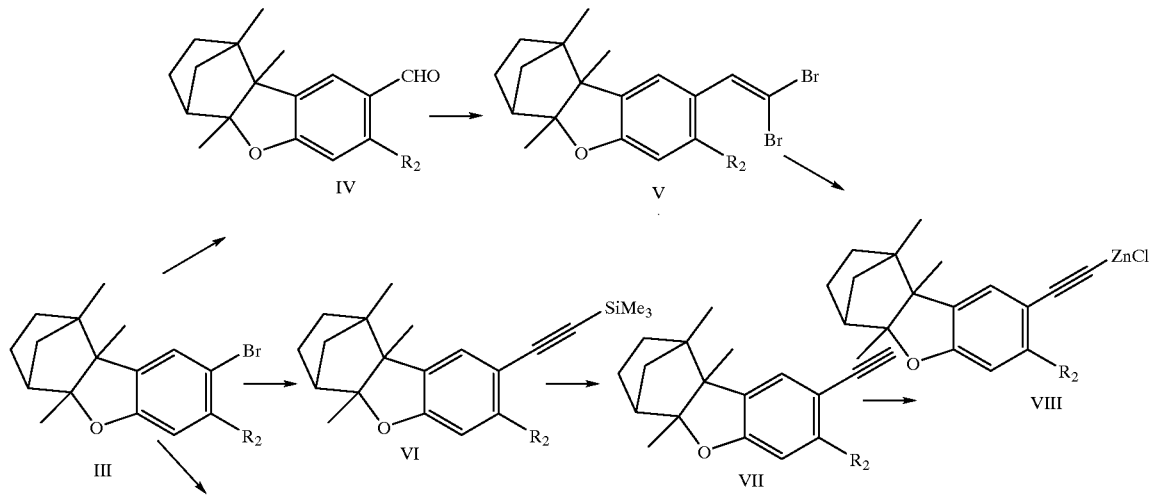

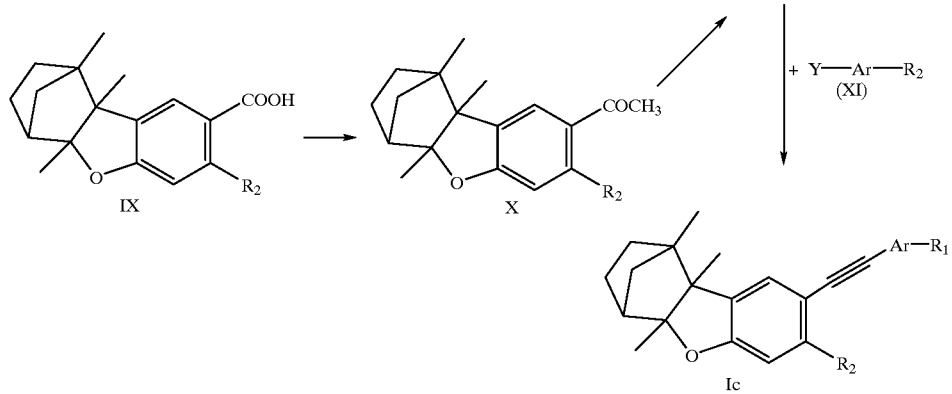

The acetylenic derivative VII is then converted into an organolithium derivative and then into the organozinc compound VIII and condensed with a halogenated derivative (iodinated or brominated) IX in the presence of a palladium catalyst, such as tetrakis(triphenylphosphine)palladium(0), in a solvent such as THF, according to the conditions described by Negishi et al. (J. Org. Chem., 1977, vol. 42, 1821–1823).

The compounds of formula Id, Ie, If and Ig are obtained according to the synthetic routes described in FIG. 2 hereinbelow.

The compounds of formula Id can be obtained by reacting an activated form of the benzoic acid, such as an acid chloride XII, for example, with a phenolic compound XIII in anhydrous medium, in an organic solvent such as THF, in the presence of a tertiary amine.

The compounds of formula Ie can be obtained under the same conditions as for the preparation of the compounds Id by replacing the phenolic derivative by a thiophenolic derivative XIV.

The compounds of structure If are obtained under the same conditions as for the preparation of the derivatives Id by replacing the phenolic derivative XIII by an arylaminated derivative XV.

The compounds of formula Ig can be obtained from the compounds of formula If by reaction with is Lawesson's reagent.

FIG. 2

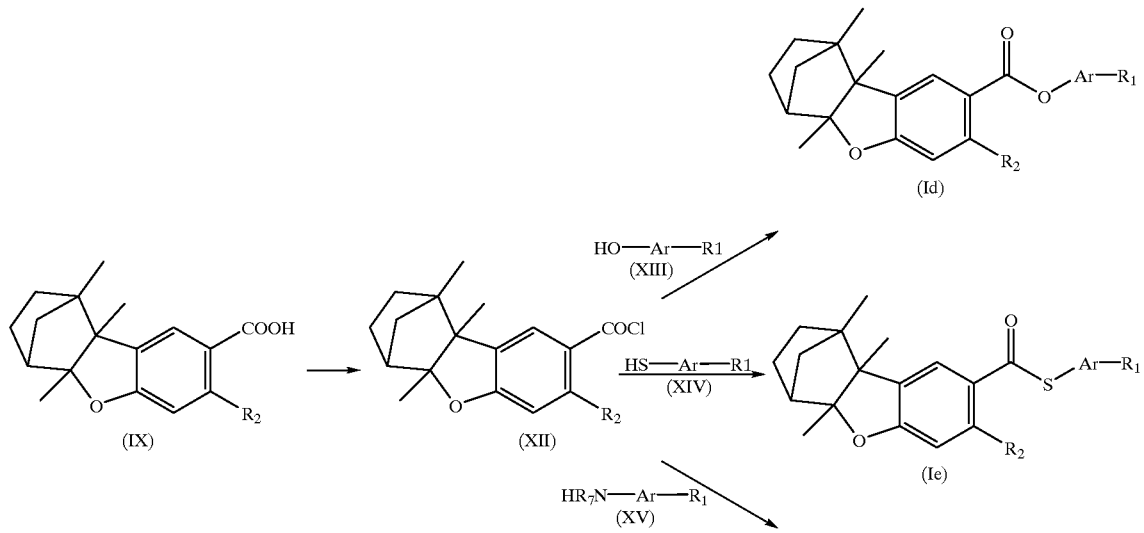

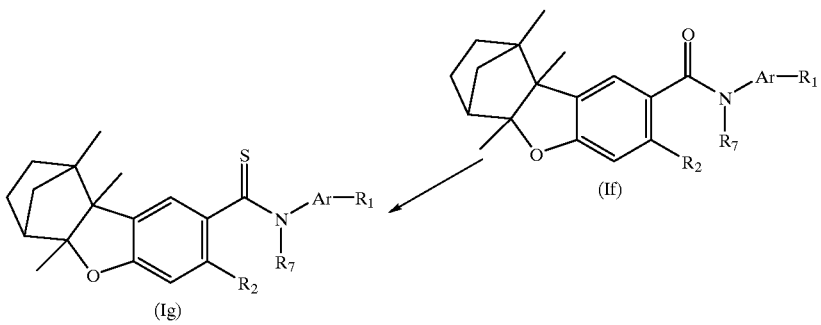

(If)

(Ig)

The compounds of formula Ih can be obtained from the brominated derivatives of formula XVI with a phenol, thiophenol or aminated compound of formula XVII in the presence of potassium carbonate or of an alkali metal hydride, such as sodium hydride, or by phase transfer.

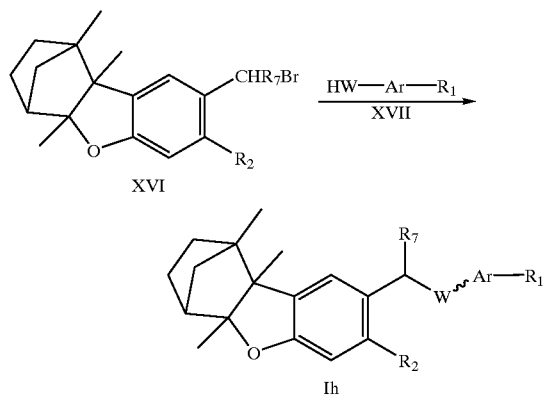

During all these reactions mentioned hereinabove, $R_1$, $R_2$, $R_7$ and $R_8$ have the meanings described in the formula I or are protective groups for the functional groups compatible with the reaction conditions. The protective groups employed are those described in the book "Protecting groups in organic synthesis" by T. W. Greene, published by John Wiley and Sons (1981).

For the preparation of the compounds of general formula I, it might be possible to be induced to carry out conventional reactions of organic chemistry, such as, for example, those described hereinbelow, by resorting to methods described in "Advanced Organic Chemistry" by J. March; John Wiley and Sons, 1985. Some conventional transformations for the conversion of functional groups are presented hereinbelow:

| | | |
|---|---|---|
| carboxylic acid | → | ester |
| ester | → | carboxylic acid |
| acid | → | acid chloride |
| acid chloride | → | amide |
| acid | → | amide |
| acid | → | alcohol |
| alcohol | → | aldehyde |
| amide | → | amine |
| thiol | → | thioether |
| thioether | → | sulphoxide |
| thioether | → | sulphone |

These compounds exhibit an agonist activity with respect to the expression of one or more biological markers in the test of differentiation of mouse embryonic teratocarcinoma cells (F9) (Skin Pharmcol., 3, p. 256–267, 1990) and/or with respect to the in vitro differentiation of human keratinocytes (Skin Pharmcol., 3, p. 70–85, 1990). Their activities with respect to these receptors can also be measured in cell transactivation tests using previously transfected recombinant RAR or RXR receptors (Biochemical and Biophysical Research Communication, 1992, vol. 186, 977–983; Journal of Medicinal Chemistry, 1994, 37, 408–414). The compounds of this series can exhibit, according to the nature of the linker and of the aromatic nucleus, a selectivity for the subtype of RAR-alpha receptors. Their affinities for nuclear receptors of retinoic acid (RARs) are measured according to the method described previously (Journal of Medicinal Chemistry, 1995, vol. 38, 4993–5006).

These compounds are also characterized by pharmacological activities in the test of inhibition of ornithine decarboxylase after induction by TPA in the mouse (Cancer Research, 1978, 38, 793–801).

The compounds according to the invention are particularly well suited to the following fields of treatment:

1) For treating dermatological conditions linked to a disorder of keratinization involving differentiation and proliferation, in particular for treating acne vulgaris, comedonic or polymorphic acne, acne rosacea, nodulocystic acne, acne conglobata, senile acne and secondary acnes such as solar, drug or occupational acne, 2) For treating other types of disorders of keratinization, in particular ichthyoses, ichthyosiform conditions, Darier's disease, palmoplantar keratoderma, leucoplakia and leucoplakiform conditions or cutaneous or mucosal (oral) lichen, 3) For treating other dermatological conditions linked to a disorder of keratinization with an inflammatory and/or immunoallergic component and, in particular, all forms of psoriasis, either cutaneous, mucosal or ungual, and even psoriatic rheumatism, or alternatively cutaneous atopy, such as eczema, or respiratory atopy or alternatively gingival hypertrophy; the compounds can also be used in certain inflammatory conditions which do not show disorder of keratinization, 4) For treating all dermal or epidermal proliferations, whether they are benign or malignant and whether they are or are not of viral origin, such as common warts, flat warts and epidermodysplasia verruciformis, florid or oral papillomatoses and the proliferations which can be induced by ultraviolet radiation, in particular in the case of basal cell and prickle cell epithelioma, 5) For treating other dermatological disorders, such as bullous dermatoses and collagen diseases, 6) For treating certain ophthalmological disorders, in particular corneopathies, 7) For repairing or controlling ageing of the skin, whether photoinduced or chronologic or for reducing actinic keratoses and pigmentations or any pathology associated with chronologic or actinic ageing,
8) For preventing or treating the stigmata of epidermal and/or dermal atrophy induced by local or systemic corticosteroids, or any other form of cutaneous atrophy,
9) For preventing or treating disorders of cicatrization or for preventing or repairing stretch marks,
10) For controlling disorders of the sebaceous function such as hyperseborrhoea of acne or simple seborrhoea,
11) In the treatment or prevention of cancerous or precancerous conditions, more particularly promyelocytic leukaemias,
12) In the treatment of inflammatory conditions such as arthritis,
13) In the treatment of any condition of viral origin at the cutaneous level, such as Kaposis' syndrome, or the general level,
14) In the prevention or treatment of alopecia,
15) In the treatment of dermatological conditions with an immune component,
16) In the treatment of ailments of the cardiovascular system such as arteriosclerosis or hypertension, as well as non-insulin-dependent diabetes,
17) In the treatment of skin disorders due to exposure to U.V. radiation.

In the therapeutic fields mentioned above, the compounds according to the invention can advantageously be employed in combination with other retinoids, with vitamins D or their derivatives, with corticosteroids, in combination with antioxidants, with a-hydroxy or a-keto acids or their derivatives, or alternatively with ion-channel blockers.

Vitamins D or their derivatives is understood to mean, for example, the derivatives of vitamin $D_2$ or $D_3$ and in particular 1,25-dihydroxyvitamin $D_3$.

Antioxidants is understood to mean, for example, a-tocopherol or its derivatives, flavonoids, antioxidants of the BHT or BHA type or their derivatives, ascorbic acid or certain metal-chelating agents.

α-Hydroxy or α-keto acids or their derivatives is understood to mean, for example, lactic, malic, citric, glycolic, mandelic, tartaric, glyceric or ascorbic acids or salicylic acid derivatives or their salts, amides or esters.

Ion-channel blockers is understood to mean, for example, minoxidil (2,4-diamino-6-piperidinopyrimidine 3-oxide) and its derivatives.

Another subject of the present invention is medicinal compositions comprising at least one compound of formula (I) as defined hereinabove, one of its optical or geometrical isomers or one of its salts.

Another subject of the present invention is therefore a novel medicinal composition intended especially for treating the abovementioned conditions, characterized in that it comprises, in a pharmaceutically acceptable vehicle, at least one compound of formula (I), as defined hereinabove.

The administration of the compounds according to the invention can be carried out enterally, parenterally, topically or ocularly.

For enteral administration, the medicaments can be provided in the form of tablets, hard gelatin capsules, dragees, syrups, suspensions, solutions, powders, granules, emulsions or polymeric or lipid microspheres or nanospheres or vesicles which make possible controlled release. For parenteral administration, the compositions can be provided in the form of solutions or suspensions for infusion or for injection.

The compounds according to the invention are generally administered at a daily dose of approximately 0.01 mg/kg to 100 mg/kg by body weight in 1 to 3 intakes.

For topical administration, the pharmaceutical compositions based on compounds according to the invention are intended for treating the skin and the mucosal membranes and are provided in the form of ointments, creams, milks, salves, powders, impregnated pads, solutions, gels, sprays, lotions or suspensions. They can also be provided in the form of polymeric or lipid vesicles or nanospheres or microspheres or of polymeric patches and of hydrogels which make possible controlled release. These compositions for topical administration can be provided either in anhydrous form or in aqueous form, according to the clinical indication.

For ocular administration, they are mainly eye washes.

These pharmaceutical compositions, in particular for topical or ocular administration, contain at least one compound of formula (I) as defined above, one of its optical or geometrical isomers or one of its salts, at a concentration preferably of between 0.001 and 5% by weight with respect to the total weight of the composition.

The compounds of formula (I) according to the invention also find an application in the cosmetics field, in particular in body and hair hygiene, and especially for the treatment of skin with a tendency to develop acne, for hair regrowth and combating hair loss, for combating the greasy appearance of the skin or the hair, in protecting against the deleterious effects of sunlight or in the treatment of physiologically dry skin, and for preventing and/or for controlling photoinduced or chronologic ageing.

In the cosmetics field, the compounds according to the invention can advantageously be employed in combination with other retinoids, with D vitamins or their derivatives, with corticosteroids, in combination with compounds which control free radicals, with α-hydroxy or α-keto acids or their derivatives, or alternatively with ion-channel blockers.

The various products taken in combination with the compounds of the present invention being as defined above.

The present invention is thus also targeted at a cosmetic composition comprising, in a cosmetically acceptable vehicle, at least one compound of formula (I) as defined above, this composition being provided in particular in the form of a cream, a milk, a lotion, a gel, polymeric or lipid vesicles or nanospheres or microspheres, a soap or a shampoo.

The concentration of compound of formula (I) in the cosmetic compositions is between 0.001 and 3% by weight with respect to the total weight of the composition.

The medicinal and cosmetic compositions according to the invention can additionally contain inert or even pharmacodynamically or cosmetically active additives or combinations of these additives and especially: wetting agents; depigmenting agents such as hydroquinone, azelaic acid, caffeic acid or kojic acid; emollients; hydrating agents such as glycerol, PEG 400, thiamorpholinone and its derivatives or urea; anti-seborrhoeic or anti-acne agents such as S-carboxymethylcysteine, S-benzylcysteamine, their salts and their derivatives, or benzoyl peroxide; antibiotics such as erythromycin and its esters, neomycin, clindamycin and its esters, or tetracyclins; antifungal agents such as ketoconazole or 4,5-polymethylene-3-isothiazolinones; agents promoting hair regrowth, such as minoxidil (2,4-diamino-6-piperidinopyrimidine 3-oxide) and its derivatives, diazoxide (7-chloro-3-methyl-1,2,4-benzothiadiazine 1,1-dioxide) and phenytoin (5,4-diphenylimidazolidine-2,4-dione); non-steroidal anti-inflammatory agents; carotenoids and especially b-carotene; anti-psoriatic agents such as anthralin and its derivatives; and finally eicosa-5,8,11,14-tetraynoic and eicosa-5,8,11-trynoic acids, their esters and the amides.

The compositions according to the invention can also contain flavour enhancers, preserving agents such as the esters of para-hydroxybenzoic acid, stabilizing agents, moisture-regulating agents, pH-regulating agents, osmotic-pressure-modifying agents, emulsifying agents, UV-A and UV-B screening agents and antioxidants such as a-tocopherol, butylated hydroxyanisole or butylated hydroxytoluene.

A number of examples of the preparation of active compounds of formula (I) according to the invention, as well as examples of compositions containing them, will now be given by way of illustration and without any implied limitation.

A. COMPOUND EXAMPLES

All the products whose syntheses are described hereinbelow were characterized by proton NMR (250 MHz), mass spectrometry and elemental analysis.

Example 1a

2-Carboxaldehyde-4-thiophenecarboxylic acid 19.4 ml of ethylene glycol and 20 mg of paratoluenesulphonic acid are added to a solution of 2-carboxaldehyde-4-bromothiophene (53 g, 277 mmol) in 70 ml of benzene. The reaction mixture is brought to reflux for 10 hours and the water formed is removed using a Dean and Stark apparatus. After cooling, the organic phase is neutralized with a saturated bicarbonate solution. After treatment, 64.3 g (99%) of 2-carboxaldehyde-4-thiophene ethylene ketal are isolated in the form of an orange-coloured oil which is then dissolved in 600 ml of ethyl ether. 131 ml of butyllithium (2.5M in hexane) are added to this solution at −70°, carbon dioxide gas is then sparged into the reaction mixture for 1 h 30 min and the reaction mixture is allowed to return to room temperature overnight with stirring. The reaction mixture is poured into water and acidified to pH 1 with 6N HCl. This acidic aqueous phase is left stirring at room temperature overnight. After extracting with ethyl acetate, followed by a standard treatment and recrystallization from a hexane/Et2O mixture, 33 g (77%) of the expected derivative are isolated in the form of a white powder melting at 163–165° C.

Example 1b

4-Ethoxycarbonyl-2-thiophenecarboxaldehyde 33 g (211 mmol) of the acid obtained in 1a, in solution in 1 of DMF, are treated at room temperature with 7 g of sodium hydride (at 80% in oil) with stirring for 30 min. 19 ml (23.2 mmol) of methyl iodide are then added dropwise and the reaction mixture is left stirring overnight at room temperature. The reaction mixture is poured into ice-cold water and is then extracted with AcOEt. After standard treatment, followed by chromatography (hexane/CH2Cl2, 50/50) and then by recrystallization from hexane, 28.6 g (74%) of the derivative lb are isolated in the form of a white powder melting at 47° C.

Example 1c

Ethyl 4-hydroxymethyl-2-thiophenecarboxylate

The compound 1b (155 mmol), in solution in 300 ml of an ethanol/THF (1/1) mixture, is treated at room temperature with 2.93 g of sodium borohydride. The reaction mixture is left stirring at room temperature for 2 hours. After evaporating the solvents, adding water and extracting with ether, the organic phase is rinsed with acidic aqueous solution and then the standard treatment is carried out. 27.7 g of the derivative 1c are isolated in the form of a yellow oil.

Example 1d

Ethyl 4-bromomethyl-2-thiophenecarboxylate

The compound 1c (27.5 g, 147 mmol), in solution in toluene (280 ml) and pyridine (12 ml), is treated at 0° C. by dropwise addition of phosphorus tribromide (16.7 ml, 177 mmol) in 30 ml of toluene. The reaction mixture is left stirring at room temperature overnight. After evaporating the toluene and adding water, the aqueous phase is extracted with ethyl acetate and the phase is washed with a saturated bicarbonate solution, rinsed, dried and evaporated. After chromatography (hexane/CH2Cl2, 50/50), 32.1 g (88%) of the derivative Id are isolated in the form of a yellowish oil.

Example 1e

Diethyl 2-ethoxycarbonyl-4-thiophenemethylphosphonate

The derivative 1d is treated with 25 ml of triethyl phosphite and is heated at 110° C. for 5 hours. After chromatography (CH2Cl2/Et2O, 90/10), 38.7 g (98%) of the derivative 1e are isolated in the form of a yellow oil.

Example 2

Z and E geometrical isomers of ethyl [2-(1,2,3,4,4a,9b-hexahydro-1,4a,9b-trimethyl-1,4-methanodibenzofuran-8-yl)-1-propenyl]-4-thiophenecarboxylate The mixture composed of (1.74 g, 6.43 mmol) of (−)-1,2,3,4,4a,9b-hexahydro-1,4a,9b-trimethyl-1,4-methanodibenzofuran-8-yl methyl ketone described in EP 709,382, the phosphonate obtained in Example 1e and 280 mg of crown ether (15-crown-5) in 40 ml of THF is added dropwise to a round-bottomed flask containing a suspension of 233 mg of NaH (80% in oil) in 2 ml of THF. The reaction is left stirring at room temperature overnight. The reaction mixture is poured into ice-cold water, is acidified with 6N hydrochloric acid and is extracted with ethyl ether. After a standard treatment, followed by chromatography (hexane/CH2Cl2, 70/30), 1.67 g of the mixture of the Z and E geometrical isomers of ethyl [2-(1,2,3,4,4a,9b-hexahydro-1,4a,9b-trimethyl-1,4-methanodibenzofuran-8-yl)-1-propenyl]-4-thiophenecarboxylate are isolated in the form of a yellowish oil.

Example 3

(−)-2-[(Z)-2-(1,2,3,4,4a,9b-Hexahydro-1,4a,9b-trimethyl-1,4-methanodibenzofuran-8-yl)-1-propenyl]-4-thiophenecarboxylic acid 1.61 g (3.8 mmol) of the mixture of esters obtained in Example 2, in solution in 30 ml of EtOH, are treated with 1.68 g of sodium hydroxide and heated for 1 hour at reflux. After evaporating the ethanol and adding water, the mixture is acidified with 2N HCl and extracted with ethyl ether. The standard treatment, followed by preparative HPLC chromatography (C18 column, eluent CH3CN/0.1% of trifluoroacetic acid in water, 65/35) [lacuna] 0.62 g (42%) of the expected derivative 3 in the form of a white powder melting at 220–222° C.; $\alpha_D$=−45° (c=1, DMF).

Example 4

(+)-2-[(E)-2-(1,2,3,4,4a,9b-Hexahydro-1,4a,9b-trimethyl-1,4-methanodibenzofuran-8-yl)-1-propenyl]-4-thiophenecarboxylic acid HPLC chromatography, carried out on the mixture of acids obtained in Example 3, also makes it possible to obtain 0.27 g (18%) of the E isomer in the form of a white powder melting at 200° C.; αD=+17.3° (c=1, DMF).

Example 5
(+)-2-[(Z)-2-(1,2,3,4,4a,9b-Hexahydro-1,4a,9b-trimethyl-1,4-methanodibenzofuran-8-yl)-1-propenyl]-4-thiophenecarboxylic acid 2.07 g (7.65 mmol) of (+)-[1,2,3,4,4a,9b-hexahydro-1,4a,9b-trimethyl-1,4-methanodibenzofuran-8-yl methyl ketone] are treated with diethyl 4-bromomethyl-2-thiophenecarboxylate (2.81 g, 9.18 mmol) under the conditions described in Example 2. After chromatography on silica, 1.41 g (68%) of the Z/E mixture of the ethyl [2-(1,2,3,4,4a,9b-hexahydro-1,4a,9b-trimethyl-1,4-methanodibenzofuran-8-yl)-1-propenyl]-4-thiophenecarboxylate compounds are isolated in the form of a white powder. This mixture is saponified and purified by HPLC under the conditions described in Example 3. 0.3 g (14%) of the compound S is then isolated in the form of a white powder melting at 187–189° C.; $\alpha_D$=+48° (c=1, DMF)

Example 6
(−)-2-[(E)-2-(1,2,3,4,4a,9b-Hexahydro-1,4a,9b-trimethyl-1,4-methanodibenzofuran-8-yl)-1-propenyl]-4-thiophenecarboxylic acid HPLC purification on the mixture of acids obtained in Example 5 also makes it possible to obtain 0.7 g of the derivative 6 in the form of a white powder melting at 212–214° C.; $\alpha_D$=−15° (c=1, DMF)

Example 7
Methyl 4-[-2-(1,2,3,4,4a,9b-hexahydro-1,4a,9b-trimethyl-1,4-methanodibenzofuran-8-yl)-ethynyl]benzoate 7.6 ml of n-butyllithium (1.6M) in hexane are added dropwise to a solution of 2.8 g (11 mmol) of the compound (−)-8-ethynyl-(1,2,3,4,4a,9b-hexahydro-1,4a,9b-trimethyl-1,4-methanodibenzofuran), described in EP 709,382, in 30 ml of THF at 0° C. and the mixture is stirred for 30 minutes at room temperature. The mixture is then cooled to 0° C. and 1.66 g (12 mmol) of ZnCl2 are added and then the mixture is stirred for 1 hour at room temperature.

2.56 g (2.2 mmol) of tetrakis(triphenylphosphine)palladium(0) and 2.91 g (11 mmol) of methyl 4-iodobenzoate are introduced into a three-necked flask containing 30 ml of THF. This solution is stirred at room temperature for 30 minutes and then the organozinc solution prepared previously is added to it. The reaction mixture is stirred at room temperature for 4 days. The reaction mixture is poured into 200 ml of 3N hydrochloric acid at 0° C. After extracting this mixture with ether, followed by the standard treatment and by chromatography on silica (hexane/dichloromethane, 80/20), 2.34 g (55%) of the expected derivative are isolated, which derivative melts at 155–156° C.

Example 8
(+)-4-[-2-(1,2,3,4,4a,9b-Hexahydro-1,4a,9b-trimethyl-1,4-methanodibenzofuran-8-yl)ethynyl]benzoic acid 2.33 g (6 mmol) of the ester obtained in Example 7, in 250 ml of methanol containing 2.31 g of sodium hydroxide, are heated at reflux for 5 hours. After the same treatment as in Example 3, followed by recrystallization from the ethyl acatate/hexane mixture, 1.17 g (68%) of the derivative 8 are isolated in the form of a white powder melting at 253–255° C.; $\alpha_D$=+16.3 (c=1, DMF).

Example 9
Ethyl 4-[-2-(1,2,3,4,4a,9b-hexahydro-1,4a,9b-trimethyl-1,4-methanodibenzofuran-8-yl)-ethynyl]-2-thiophenecarboxylate 2.1 g (8.3 mmol) of the alkyne (−)-8-ethynyl-1,2,3,4,4a,9b-hexahydro-1,4a,9b-trimethyl-1,4-methanodibenzofuran, described in EP 709,382, are converted to an organozinc compound and are coupled with 1.95 g (8.3 mmol) of ethyl 4-bromo-2-thiophenecarboxylate under the conditions described in Example 7. After the same treatment as in the isolation of the compound 7, followed by chromatography on silica is (hexane/dichloromethane, 70/30), 0.98 g (29%) of the derivative 9 is isolated in the form of a yellow oil.

Example 10
(+)-4-[-2-(1,2,3,4,4a,9b-Hexahydro-1,4a,9b-trimethyl-1,4-methanodibenzofuran-8-yl)ethynyl]-2-thiophenecarboxylic acid The compound obtained in Example 9 (0.96 g, 2.36 mmol) is saponified in the presence of 0.95 g of sodium hydroxide under the conditions described in Example 8. After the same treatment, followed by recrystallization from an ether/hexane mixture, 0.70 g (79%) of the expected derivative is isolated in the form of a white powder melting at 203–205° C.; $\alpha_D$=+22.2 (c=1, CHCl3).

Example 11
Benzyl 4-[(1,2,3,4,4a,9b-hexahydro-1,4a,9b-trimethyl-1,4-methanodibenzofuran-8-yl)carbonyloxy]benzoate 2.54 g (9.3 mmol) of (−)-[1,2,3,4,4a,9b-hexahydro-1,4a,9b-trimethyl-1,4-methanodibenzofuran-8-yl]carboxylic acid, described in EP 709,382, in 50 ml of toluene are treated with 1.35 ml of thionyl chloride and are heated at reflux for 4 hours. After evaporating the solvent, 4.6 g of chloride of (1,2,3,4,4a,9b-hexahydro-1,4a,9b-trimethyl-1,4-methanodibenzofuran-8-yl)carboxylic acid are isolated in the form of a beige powder.

2.15 g (9.4 mmol) of benzyl para-hydroxybenzoate in 20 ml of THF are treated with 0.31 g of sodium hydride (80% in oil). This reaction mixture is then subjected to dropwise addition of the acid chloride in solution in 30 ml of THF. After addition, the mixture is left stirring at room temperature overnight. The reaction mixture is then poured into ice-cold water and extracted with ether. After the standard treatment, followed by chromatography on silica (hexane/dichloromethane, 40/60), 4 g (91%) of the derivative 11 are isolated in the form of white crystals melting at 131–133° C.

Example 12
(+)-4-[(1,2,3,4,4a,9b-Hexahydro-1,4a,9b-trimethyl-1,4-methanodibenzofuran-8-yl)carbonyloxy]benzoic acid The benzyl ester 11 (4 g, 8.3 mmol), in solution of 50 ml dioxane, is hydrogenated in the presence of 0.8 g of palladium-on-charcoal (10%) under 5 bar of hydrogen for 1 hour 30. The reaction mixture is then filtered through celite and then evaporated to result in 3.15 g (97%) of the derivative 12 in the form of a white crystalline solid melting at 222–224° C.; $\alpha_D$=+3.7° (c=1, CHCl3).

Example 13
(−)-4-[(1,2,3,4,4a,9b-Hexahydro-1,4a,9b-trimethyl-1,4-methanodibenzofuran-8-yl)carbonyloxy]benzoic acid The same synthesis as that carried out in the case of Example 11, from (+)-(1,2,3,4,4a,9b-hexahydro-1,4a,9b-trimethyl-1,4-methanodibenzofuran-8-yl)carboxylic acid, followed by hydrogenation under the same conditions as in Example 21, results in the laevorotatory enantiomer 13 exhibiting the same physicochemical characteristics as those of the enantiomer 12; $\alpha_D$=−3.2° (c=1, CHCl3).

Example 14
Benzyl 4-[(1,2,3,4,4a,9b-hexahydro-1,4a,9b-trimethyl-1,4-methanodibenzofuran-8-yl)carboxamido]benzoate 4 g (14.8 mmol) of (−)-[1,2,3,4-tetrahydro-1,4a,9b-trimethyl-1,4-methanodibenzofuran-8-yl]carboxylic acid, described in EP 709,382, are converted to acid chloride under the conditions described in Example 11. The resulting acid chloride is placed in 50 ml of THF and is then treated by dropwise addition of a solution containing 3.36 g (14.8 mmol) of benzyl para-aminobenzoate, 2.3 ml of triethylamine and 20 mg of 4-N,N-dimethylaminopyridine. The reaction mixture is then left stirring at room temperature overnight. This mixture is then poured into ice-cold water and is then extracted with ether. The standard treatment, followed by chromatography on silica (hexane/dichloromethane, 20/80) and by recrystallization from hexane, results in 6.4 g (90%) of the derivative 14 in the form of white crystals melting at 74–76° C.

Example 15
(+)-4-[(1,2,3,4,4a,9b-Hexahydro-1,4a,9b-trimethyl-1,4-methanodibenzofuran-8-yl)carboxamido]benzoic acid 6.4 g (13 mmol) of the derivative obtained in Example 14, in solution in 60 ml of dioxane, are hydrogenated under a hydrogen pressure of 5 bar at room temperature for 1 hour. After the same treatment as in Example 12, followed by chromatography (dichloromethane/methanol, 9/1), 3.8 g (75%) of the derivative 15 are isolated in the form of a white powder melting at 298–300° C.; $\alpha_D$=+16.9° (c=1, DMF).

Example 16
(−)-4-[(1,2,3,4,4a,9b-Hexahydro-1,4a,9b-trimethyl-1,4-methanodibenzofuran-8-yl)carboxamido]benzoic acid The same synthesis as that carried out in the case of Example 14, from (+)-[1,2,3,4,4a,9b-hexahydro-1,4a,9b-trimethyl-1,4-methanodibenzofuran-8-yl]carboxylic acid, followed by hydrogenation under the same conditions as in Example 15, results in the laevorotatory enantiomer 16, which exhibits the same physicochemical characteristics as those of the dextrorotatory enantiomer 15; ($\alpha_D$=−15.5° (c=1, CHCl3).

Example 17
Benzyl 4-[(1,2,3,4,4a,9b-hexahydro-1,2,3,4-tetrahydro-1,4a,9b-trimethyl-1,4-methanodibenzofuran-8-yl)thiocarboxamido]benzoate 1.97 g (4.1 mmol) of the amide obtained in Example 14, in 20 ml of toluene, are treated with 0.83 g (2 mmol) of Lawesson's reagent and are heated at 110° C. for 2 hours 30. After evaporating to dryness, the residue is chromatographed on silica (hexane/dichloromethane, 20/80). 1.94 g (95%) of the derivative 17 are then isolated in the form of a yellow is amorphous solid.

Example 18
(+)-4-[(1,2,3,4,4a,9b-Hexahydro-1,2,3,4-tetrahydro-1,4a,9b-trimethyl-1,4-methanodibenzofuran-8-yl)thiocarboxamido]benzoic acid The benzyl ester 17 (1.92 g, 3.8 mmol), in 50 ml of methanol, is saponified in the presence of 2 g of sodium hydroxide. The mixture is heated at reflux for 3 hours 30. After the same treatment as in Example 3, followed by recrystallization from the ethyl acetate/hexane mixture, 1.25 g (79%) of derivative 18 are isolated in the form of a yellow solid melting at 234–236° C.; $\alpha_D$=+29° (c=1, CHCl3)

Example 19
(−)-4-[(1,2,3,4,4a,9b-Hexahydro-1,2,3,4-tetrahydro-1,4a,9b-trimethyl-1,4-methanodibenzofuran-8-yl)thiocarboxamido]benzoic acid The same synthesis as that carried out in the case of Example 17, from (+)-[1,2,3,4,4a,9b-hexahydro-1,2,3,4-tetrahydro-1,4a,9b-trimethyl-1,4-methanodibenzofuran-8-yl]carboxylic acid, followed by saponification under the same conditions as in Example 18, results in the laevorotatory enantiomer 19, which exhibits the same physicochemical characteristics as those of the dextrorotatory enantiomer (18); $\alpha_D$=−25° (c=1, DMF).

Example 20
Benzyl 2-hydroxy-4-[(1,2,3,4-tetrahydro-1,4a,9b-trimethyl-1,4-methanodibenzofuran-8-yl)carbonyloxy]benzoate 0.58 mg (2 mmol) of chloride of (+)-[1,2,3,4,4a,9b-hexahydro-1,2,3,4-tetrahydro-1,4a,9b-trimethyl-1,4-methanodibenzofuran-8-yl]carboxylic acid, in solution in 10 ml of THF, are coupled with benzyl 2,4-dihydroxybenzoate (0.48 g, 2 mmol) under the conditions described in Example 11. After the same treatment, followed by chromatography (heptane/dichloromethane, 20/80), 0.39 g (40%) of the derivative 20 is isolated in the form of a yellow oil.

Example 21
(+)-2-Hydroxy-4-[(1,2,3,4,4a,9b-hexahydro-1,2,3,4-tetrahydro-1,4a,9b-trimethyl-1,4-methanodibenzofuran-8-yl)carbonyloxy]benzoic acid The ester 29 (0.38 g, 0.76 mmol), in 50 ml of dioxane, is hydrogenated in the presence of 80 mg of palladium-on-charcoal (10%) under a hydrogen pressure of 5 bar for 2 hours 30 at room temperature. After the same treatment as in Example 12, followed by recrystallization from an ethyl acetate/heptane mixture, 0.18 g (58%) of the derivative 21 is isolated in the form of white crystals melting at 208–210° C.; $\alpha_D$=+3.6° (c=1, DMF).

Example 22
Benzyl 2-hydroxy-4-[(1,2,3,4-tetrahydro-1,4a,9b-trimethyl-1,4-methanodibenzofuran-8-yl)carboxamido]benzoate 1.32 g (4.5 mmol) of the chloride of (+)-[1,2,3,4-tetrahydro-1,4a,9b-trimethyl-1,4-methanodibenzofuran-8-yl]carboxylic acid in 20 ml of THF are treated with a solution containing 0.76 g (4.5 mmol) of methyl 2-hydroxy-4-aminobenzoate and 0.64 ml of triethylamine in 15 ml of THF. The reaction mixture is left stirring at room temperature for 5 hours. The reaction mixture is subsequently poured into water and extracted with ethyl ether. The standard treatment, followed by chromatography (dichloromethane/heptane, 80/20), results in 1.16 g (60%) of the derivative 22 in the form of white crystals melting at 231–233° C.

Example 23
2-Hydroxy-4-[(1,2,3,4,4a,9b-hexahydro-1,4a,9b-trimethyl-1,4-methanodibenzofuran-8-yl)carboxamido]benzoic acid The derivative 22 (0.67 mg, 1 mmol) is saponified with with 5 ml of a 2N methanolic sodium hydroxide solution at reflux for 3 hours. After the same treatment as in Example 4, followed by chromatography on silica (dichloromethane/THF, 95/5), 0.2 g (51%) of the derivative 23 is isolated in the form of a white crystalline solid melting at 235–236° C.; $\alpha_D$=−14.2° (c=1, DMF).

Example 24
Methyl 2-hydroxy-4-[(1,2,3,4,4a,9b-hexahydro-1,4a,9b-trimethyl-1,4-methanodibenzofuran-8-yl)thiocarboxamido]benzoate 0.93 g (2.2 mmol) of the amide 22 in 20 ml of toluene are treated with 0.46 g of Lawesson's reagent under the conditions described in Example 17, to result, after the same treatment, followed by chromatography on silica (dichloromethane/heptane, 9/1), in 1.15 g (97%) of the derivative 24 in the form of an orange amorphous solid.

Example 25

2-Hydroxy-4-[(1,2,3,4,4a,9b-hexahydro-1,4a,9b-trimethyl-1,4-methanodibenzofuran-8-yl)-thiocarboxamido]benzoic acid The methyl ester 24 (1.13 g, 2.6 mmol) is saponified under the conditions described in Example 18. After the same treatment, followed by chromatography on silica (dichloromethane/ethyl acetate, 9/1) and by recrystallization from heptane, 0.58 g (53%) of the derivative 25 is isolated in the form of yellow crystals melting at 213–214° C.; $\alpha_D = -22.8°$ (c=1, DMF)

B. FORMULATION EXAMPLES

1) ORAL ROUTE (a) The following composition is prepared in the

| | |
|---|---|
| Compound of Example 9 | 0.005 g |
| Pregelatinized starch | 0.265 g |
| Microcrystalline cellose | 0.300 g |
| Lactose | 0.200 g |
| Magnesium stearate | 0.030 g |

For the treatment of acne, 1 to 3 tablets per day are administered to an adult individual for 3 to 6 months, depending on the seriousness of the case under treatment.

(b) A suspension to be taken orally, intended to be packaged in 5 ml phials, is prepared:

| | |
|---|---|
| Compound of Example 10 | 0.050 g |
| Glycerol | 0.500 g |
| 70% Sorbitol | 0.500 g |
| Sodium saccharinate | 0.010 g |
| Methyl para-hydroxybenzoate | 0.040 g |
| Flavour q.s. | |
| Purified water q.s. for | 5 ml |

For the treatment of acne, one phial per day is administered to an adult individual for 3 months, depending on the seriousness of the case under treatment.

(c) The following formulation, intended to be packaged in gelatine capsules, is prepared:

| | |
|---|---|
| Compound of Example 15 | 0.025 g |
| Maize starch | 0.060 g |
| Lactose q.s. for | 0.300 g |

The gelatin capsules used are composed of gelatin, titanium oxide and a preservative.

In the treatment of psoriasis, 1 gelatin capsule per day is administered to an adult individual for 30 days.

2) TOPICAL ROUTE (a) The following non-ionic water-in-oil cream is prepared:

| | |
|---|---|
| Compound of Example 9 | 0.100 g |
| Mixture of emulsifying lanolin alcohols and of refined waxes and oils, sold by the company BDF under the name "Anhydrous eucerin" | 39.900 g |
| Methyl para-hydroxybenzoate | 0.075 g |
| Propyl para-hydroxybenzoate | 0.075 g |
| Sterile demineralized water q.s. for | 100.000 g |

This cream is applied to a psoriatic skin 1 to 2 times per day for 30 days.

(b) A gel is prepared by producing the following formulation:

| | |
|---|---|
| Compound of Example 9 | 0.050 g |
| Erythromycin base | 4.000 g |
| Butylated hydroxytoluene | 0.050 g |
| Hydroxypropylcellulose, sold by the company Hercules under the name of "Klucel HF" | 2.000 g |
| Ethanol (at 95°) q.s. for | 100.000 g |

This gel is applied to a skin affected by dermatosis or by acne 1 to 3 times per day for 6 to 12 weeks, depending on the seriousness of the case under treatment.

(c) An antiseborrhoeic lotion is prepared by mixing the following ingredients:

| | |
|---|---|
| Compound of Example 10 | 0.030 g |
| Propylene glycol | 5.000 g |
| Butylated hydroxytoluene | 0.100 g |
| Ethanol (at 95°) q.s. for | 100.000 g |

This lotion is applied twice per day to a seborrhoeic scalp and a significant improvement is observed within a period of between 2 and 6 weeks.

(d) A cosmetic composition to counter the harmful effects of the sun is prepared by mixing the following ingredients:

| | |
|---|---|
| Compound of Example 12 | 1.000 g |
| Benzylidenecamphor | 4.000 g |
| Fatty acid triglycerides | 31.000 g |
| Glyceryl monostearate | 6.000 g |
| Stearic acid | 2.000 g |
| Cetyl alcohol | 1.200 g |
| Lanolin | 4.000 g |
| Preservatives | 0.300 g |
| Propylene glycol | 2.000 g |
| Triethanolamine | 0.500 g |
| Fragrance | 0.400 g |
| Demineralized water q.s. for | 100.000 g |

This composition is applied daily. It makes it possible to combat photoinduced ageing.

(e) The following non-ionic oil-in-water cream is prepared:

| | |
|---|---|
| Compound of Example 15 | 0.500 g |
| Vitamin D3 | 0.020 g |
| Cetyl alcohol | 4.000 g |
| Glyceryl monostearate | 2.500 g |
| PEG 50 stearate | 2.500 g |
| Karite butter | 9.200 g |
| Propylene glycol | 2.000 g |
| Methyl para-hydroxybenzoate | 0.075 g |
| Propyl para-hydroxybenzoate | 0.075 g |
| Sterile demineralized water q.s. for | 100.000 g |

This cream is applied to a psoriatic skin 1 to 2 times per day for 30 days.

(f) A topical gel is prepared by mixing the following ingredients:

| | |
|---|---|
| Compound of Example 18 | 0.050 g |
| Ethanol | 43.000 g |
| α-Tocopherol | 0.050 g |
| Carboxyvinyl polymer, sold under the name "Carbopol 941" by the company "Goodrich" | 0.500 g |
| Triethanolamine, as a 20% by weight aqueous solution | 3.800 g |
| Water | 9.300 g |
| Propylene glycol q.s. for | 100.000 g |

This gel is applied in the treatment of acne 1 to 3 times per day for 6 to 12 weeks, depending on the seriousness of the case under treatment.

(g) A hair lotion for combating hair loss and for promoting hair regrowth is prepared by mixing the following ingredients:

| | |
|---|---|
| Compound of Example 19 | 0.05 g |
| Compound sold under the name "Minoxidil" | 1.00 g |
| Propylene glycol | 20.00 g |
| Ethanol | 34.92 g |
| Polyethylene glycol (molecular mass = 400) | 40.00 g |
| Butylated hydroxyanisole | 0.01 g |
| Butylated hydroxytoluene | 0.02 g |
| Water q.s. for | 100.00 g |

This lotion is applied twice per day for 3 months to a scalp which has undergone significant hair loss.

(h) An anti-acne cream is prepared by mixing the following ingredients:

| | |
|---|---|
| Compound of Example 21 | 0.050 g |
| Retinoic acid | 0.010 g |
| Mixture of glyceryl and polyethylene glycol stearates (75 mol), sold under the name of "Gelot 64" by the company "Gattefosse" | 15.000 g |
| Kernel oil polyoxyethylenated with 6 mol of ethylene oxide, sold under the name of "Labrafil M2130 CS" by the company "Gattefosse" | 8.000 g |
| Perhydrosqualene | 10.000 g |
| Preservatives | q.s. |
| Polyethylene glycol (molecular mass = 400) | 8.000 g |
| Disodium salt of ethylenediaminetetraacetic acid | 0.050 g |
| Purified water q.s. for | 100.00 g |

This cream is applied to a skin affected by dermatosis or by acne 1 to 3 times per day for 6 to 12 weeks.

(i) An oil-in-water cream is prepared by producing the following formulation:

| | |
|---|---|
| Compound of Example 21 | 0.020 g |
| Betamethasone 17-valerate | 0.050 g |
| S-Carboxymethylcysteine | 3.000 g |

| | |
|---|---|
| Polyoxyethylene stearate (40 mol of ethylene oxide), sold under the name of "Myrj 52" by the company "Atlas" | 4.000 g |
| Sorbitan monolaurate, polyoxyethylene with 20 mol of ethylene oxide, sold under the name of "Tween 20" by the company "Atlas" | 1.800 g |
| Mixture of glyceryl mono- and distearate, sold under the name of "Geleol" by the company "Gattefosse" | 4.200 g |
| Propylene glycol | 10.000 g |
| Butylated hydroxyanisole | 0.010 g |
| Butylated hydroxytoluene | 0.020 g |
| Cetostearyl alcohol | 6.200 g |
| Preservatives | q.s. |
| Perhydrosqualene | 18.000 g |
| Mixture of caprylic/capric triglycerides sold under the name of "Miglyol 812" by the company "Dynamit Nobel" | 4.000 g |
| Triethanaolamine (99% by weight) | 2.500 g |
| Water q.s. for | 100.000 g |

This cream is applied 2 per day for 30 days to a skin affected by dermatosis.

(j) The following cream of oil-in-water type is prepared:

| | |
|---|---|
| Lactic acid | 5.000 g |
| Compound of Example 22 | 0.020 g |
| Polyoxyethylene stearate (40 mol of ethylene oxide), sold under the name of "Myrj 52" by the company "Atlas" | 4.000 g |
| Sorbitan monolaurate, polyoxyethylene with 20 mol of ethylene oxide, sold under the name of Tween 20" by the company "Atlas" | 1.800 g |
| Mixture of glyceryl mono- and distearate, sold under the name of "Geleol" by the company "Gattefosse" | 4.200 g |
| Propylene glycol | 10.000 g |
| Butylated hydroxyanisole | 0.010 g |
| Butylated hydroxytoluene | 0.020 g |
| Cetostearyl alcohol | 6.200 g |
| Preservatives | q.s. |
| Perhydrosqualene | 18.000 g |
| Mixture of caprylic/capric triglycerides, sold under the name of "Miglyol 812" by the company "Dynamit Nobel" | 4.000 g |
| Water q.s. for | 100.000 g |

This cream is applied once per day. It helps in combating ageing, whether photoinduced or chronologic.

What is claimed is:

1. A compound of general formula (I):

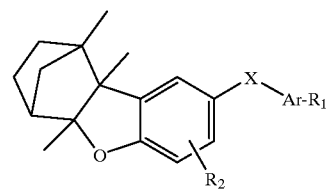

(I)

in which, Ar is selected from the group consisting of the following radicals:

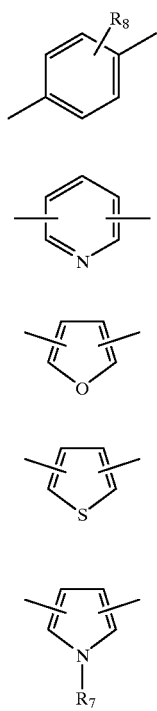

$R_7$ and $R_8$ are defined below,

X is a radical or bonds selected from the group consisting of formula (a)–(g), which can be read in both directions:

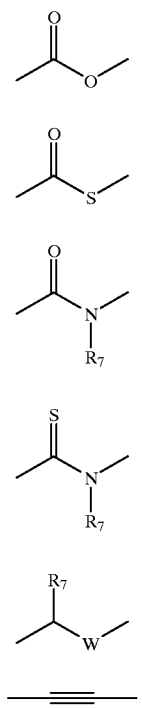

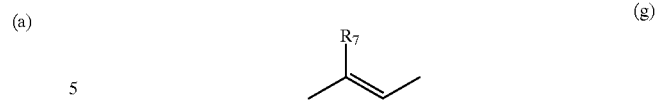

$R_1$ represents
(i) a hydrogen atom,
(ii) the —$CH_3$ radical,
(iii) the —O—$R_3$ radical,
(iv) the —$CH_2$—O—$R_3$ radical,
(v) the —O($CH_2$)$_m$—(CO)$_n$—$R_4$ radical,
(vi) the —CO—$R_5$ radical
(vii) the —CO—O—R radical $R_2$ is a hydrogen atom or a —($CH_2$)$_n$—O—$R_3$ radical, m and n and $R_3$ to $R_6$ are defined below, W is an oxygen atom, a S(O)$_p$ radical or a N—$R_7$ radical, $R_7$ is defined below, $R_3$ is a hydrogen atom, a lower alkyl radical or a —CO—$R_9$ radical, $R_9$ is defined below, $R_4$ is a lower alkyl radical or a heterocycle, $R_5$ is a hydrogen atom, a lower alkyl radical or an —N(r',r'') radical, in which r' and r'', which are identical or different, are selected from the group consisting of a hydrogen atom, a lower alkyl radical, a mono- or polyhydroxyalkyl radical, an optionally substituted aryl radical or an amino acid, and a peptide or sugar residue or alternatively r' and r'', taken together, form a heterocycle, $R_6$ is selected from the group consisting of a hydrogen atom, a linear or branched alkyl radical having from 1 to 20 carbon atoms, an alkenyl radical, a mono- or polyhydroxyalkyl radical, an optionally substituted aryl or aralkyl radical, and a sugar, amino acid or peptide residue, $R_7$ is a hydrogen atom or a lower alkyl radical, $R_8$ is a —($CH_2$)$_n$—O—$R_3$ radical, wherein $R_3$ is defined above, $R_9$ is a hydrogen atom, a lower (lacuna) radical or an aryl radical, m is an integer equal to 1, 2 or 3, n is an integer equal to 0 or 1, and the optical and geometrical isomers of the said pure compounds, mixtures thereof and pharmaceutically acceptable salts thereof.

2. A compound according to claim 1, having the general formula (Ia):

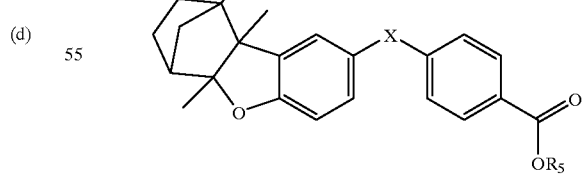

in which,

X is selected from the group consisting of (c), (d), (f) and (g), wherein (c), (d), (f), (g) and $R_6$ are defined in claim 1.

3. A compound according to claim 1, which is selected from the following compounds:

Ethyl 2-[(E)-2-(1,2,3,4,4a,9b-hexahydro-1,4a,9b-trimethyl-1,4-methanodibenzofuran-8-yl)-1-propenyl]-4-thiophenecarboxylate, 2-[(E)-2-(1,2,3,4,4a,9b-Hexahydro-1,4a,9b-trimethyl-1,4-methanodibenzofuran-8-yl)-1-propenyl]-4-thiophenecarboxylic acid, 2-[(E)-2-(1,2,3,4,4a,9b-Hexahydro-1,4a,9b-trimethyl-1,4-methanodibenzofuran-8-yl)-1-propenyl]-5-thiophenecarboxylic acid, 6-[(E)-2-(1,2,3,4,4a,9b-Hexahydro-1,4a,9b-trimethyl-1,4-methanodibenzofuran-8-yl)-1-propenyl]nicotinic acid, Methyl 4-[3-(1,2,3,4,4a,9b-hexahydro-1,4a,9b-trimethyl-1,4-methanodibenzofuran-8-yl)ethynyl]benzoate, 4-[3-(1,2,3,4,4a,9b-Hexahydro-1,4a,9b-trimethyl-1,4-methanodibenzofuran-8-yl)ethynyl]benzoic acid, 4-[-2-(1,2,3,4,4a,9b-Hexahydro-1,4a,9b-trimethyl-1,4-methanodibenzofuran-8-yl)ethynyl]-2-thiophenecarboxylic acid, 6-[-2-(1,2,3,4,4a,9b-Hexahydro-1,4a,9b-trimethyl-1,4-methanodibenzofuran-8-yl)ethynyl]nicotinic acid, Methyl 4-[3-(1,2,3,4,4a,9b-hexahydro-1,4a,9b-trimethyl-1,4-methanodibenzofuran-8-yl)carbonyloxy]benzoate, 4-[3-(1,2,3,4,4a,9b-Hexahydro-1,4a,9b-trimethyl-1,4-methanodibenzofuran-8-yl)carbonyloxy]benzoic acid, Benzyl 4-[(1,2,3,4,4a,9b-hexahydro-1,4a,9b-trimethyl-1,4-methanodibenzofuran-8-yl)carboxamido]benzoate, 4-[(1,2,3,4,4a,9b-Hexahydro-1,4a,9b-trimethyl-1,4-methanodibenzofuran-8-yl)carboxamido]benzoic acid, Methyl 6-[(1,2,3,4,4a,9b-hexahydro-1,4a,9b-trimethyl-1,4-methanodibenzofuran-8-yl)carboxamido]-2-hydroxybenzoate, 6-[(1,2,3,4,4a, 9b-Hexahydro-1,4a,9b-trimethyl-1,4-methanodibenzofuran-8-yl)carboxamido]-2-hydroxybenzoic acid, Methyl 4-[(1,2,3,4,4a,9b-hexahydro-1,4a,9b-trimethyl-1,4-methanodibenzofuran-8-yl)thiocarboxamido]benzoate acid, and 4-[(1,2,3,4,4a,9b-Hexahydro-1,4a,9b-trimethyl-1,4-methanodibenzofuran-8-yl)thiocarboxamido]benzoic acid.

4. A method of therapy which comprises the administration of at least one compound of general formula (I) according to claim 1.

5. A method of therapy according to claim 4, wherein said therapy is selected from the group consisting of treatment of a dermatological condition linked to a disorder of keratinization involving differentiation and proliferation, treatment of non-differentiation or proliferation keratinization disorders; treatment of a dermatological condition linked to a disorder of keratinization having an inflammatory and/or immunoallergic component an inflammatory condition which does not show disorder of keratinization; treatment of a malignant or non-malignant, viral or non-viral, dermal or epidermal proliferations treatment of bulbous dermatoses and collagen diseases; treatment of ophthalmological disorders; repairing or controlling ageing of the skin; preventing or treating the stigmata of epidermal and/or dermal atrophy induced by local or systemic corticosteroids, cutaneous atrophy; preventing or treating disorders of cicatrization preventing or repairing stretch marks; controlling disorders of the sebaceous function; the treatment or prevention of cancerous or precancerous conditions; the treatment of inflammatory conditions; the treatment of any condition of viral origin at the cutaneous or general level; the prevention or treatment of alopecia; the treatment of dermatological conditions having an immune component; the treatment of ailments of the cardiovascular system such as arteriosclerosis or hypertension, and the treatment of non-insulin-dependent diabetes.

6. A pharmaceutical composition, which comprises at least one compound of general formula (I) according to claim 1 and one pharmaceutically acceptable vehicle.

7. A composition according to claim 6, wherein the concentration of compound(s) of general formula (I) is between 0.001% and 5% by weight with respect to the total weight of the composition.

8. A cosmetic composition, which comprises a compound of general formula (I) according to claim 1 and a cosmetically acceptable vehicle.

9. A composition according to claim 8, wherein the concentration of compound(s) of general formula (I) is between 0.001% and 3% by weight with respect to the total weight of the composition.

10. The method of claim 5, wherein said keratinization disorder is selected from the group consisting of acne vulgaris, comedonic or polymorphic acne, acne rosacea, nodulocystic acne, acne conglobata, senile acne, secondary acne, solar, drug or occupational acne, ichthyoses, ichthyosiform conditions, Darier's disease, palmoplantar keratoderma, leucoplakia or leucoplakiform conditions, and cutaneous or mucosal lichens.

11. The method of claim 5, wherein said keratinization disorder having an inflammatory and/or immunoallergic component is selected from the group consisting of cutaneous, mucosal or ungual, psoriasis, psoriatic rheumatism, cutaneous atopy, eczema, respiratory atopy, and gingival hypertrophy.

12. The method of claim 5, wherein said dermal or epidermal proliferations are selected from the group consisting of common warts, flat warts, epidermodysplasia, verruciformis, florid or oral papillomatoses, proliferations induced by ultraviolet light, and basal cell or prickle cell epithelioma.

13. The method of claim 5, wherein said aging of the skin is photoinduced or chronologic.

14. The method of claim 5, wherein said disorder of sebaceous function is hyperseborrhoea of acne or simple seborrhoea.

15. The method of claim 5, wherein said precancerous condition is promyeolocytic leukemia.

16. The method of claim 5, wherein said inflammatory condition is arthritis.

17. The method of claim 5, wherein said cardiovascular system disorder is arteriosclerosis or hypertension.

* * * * *